US006800489B2

(12) United States Patent  (10) Patent No.: US 6,800,489 B2
Dooley  (45) Date of Patent:  Oct. 5, 2004

(54) ELECTROSPRAY TANDEM MASS SPECTROMETRY OF TRANSITION METAL DIIMINE COMPLEXES OF AMINO ACIDS, α-HYDROXYKETONES AND HEXOSE PHOSPHATES FOR NEWBORN SCREENING

(75) Inventor: Kent C. Dooley, Seabright (CA)

(73) Assignee: Izaak Walton Killam Health Center, Halifax (CA)

( * ) Notice: Subject to any disclaimer, the term of this patent is extended or adjusted under 35 U.S.C. 154(b) by 56 days.

(21) Appl. No.: 10/163,625

(22) Filed: Jun. 5, 2002

(65) Prior Publication Data

US 2003/0228704 A1 Dec. 11, 2003

(51) Int. Cl.$^7$ .......................... G01N 24/00; G01N 33/20

(52) U.S. Cl. .......................... 436/173; 436/63; 436/73; 436/74; 436/80; 436/81; 436/84; 436/86; 436/128; 436/161; 436/94; 250/281; 250/282

(58) Field of Search .............................. 436/63, 73, 74, 436/80, 81, 84, 86, 89, 128, 161, 173, 94, 95; 250/281, 282, 288

(56) References Cited

U.S. PATENT DOCUMENTS

| 5,581,286 | A | 12/1996 | Hayes et al. ................... 436/84 |
| 6,177,419 | B1 | 1/2001 | Campbell et al. ............ 514/183 |
| 6,258,605 | B1 | 7/2001 | Chace .......................... 436/86 |
| 6,451,611 | B1 * | 9/2002 | Simonsen et al. ............. 436/94 |
| 6,455,321 | B1 * | 9/2002 | Chace ......................... 436/173 |
| 2002/0102737 | A1 * | 8/2002 | Millington et al. ............ 436/94 |
| 2003/0199102 | A1 * | 10/2003 | Ostrup ....................... 436/173 |

FOREIGN PATENT DOCUMENTS

WO  WO 02/10740 A2  2/2002

OTHER PUBLICATIONS

"The Application of Tandem Mass Spectrometry to Neonatal Screening for Inherited Disorders of Intermediary Metabolism" by Chace et al., Annu. Rev. Genomics Hum. Genet., 2002, 3:17–45.
"Quantitative Electrospray Ionization Mass Spectrometric Studies of Ternary Complexes of Amino Acids with $CU^2+$ and Phenanthroline" by Gatlin et al., J. Mass Spectrom., 35, 172–177 (2000).
"Evaluation of Metal Complexation as an Alternative to Protonation for Electrospray Ionization of Pharmaceutical Compounds" by Alvarez et al., J. Am Soc. Mass Spectrom., 1998, 9, 463–472.
"Metal Complexation Reactions of Quinolone Antibiotics in a Quadrupole Ion Trap" by Alvarez et al., Anal. Chem., 1997, 69, 1147–1155.
"The Use of Electrospray Mass Spectrometry in the Detection and Determination of Molecules of Biological Significance" by Smyth., Trends in Analytical Chemistry, vol. 18, No. 5, 1999, 335–346.

"Stereochemical Differentiation of Mannose, Glucose, Galactose, and Talose Using Zinc(II) Diethylenetriamine and ESI–Ion trap Mass Spectrometry" by Gaucher et al., Anal. Chem., 1998, 70, 3009–3014.
Jensen et al., Neonatal Screening for Galactosemia by Quantitative Analysis of Hexose Monophosphates Using Tandem Mass Spectrometry: A Retrospective Study; Clinical Chemistry, 47:8, pp. 1364–1372 (2001).
Gatlin et al., Gas–phase Complexes of Amino Acids with CU(II) and Diimine Ligands, Part 1. Aliphatic and Aromatic Amino Acids, Journal ofmass Spectrometry, vol. 30, pp. 1605–1616 (1995).
Gatlin et al., Gas–phase Complexes of Amino Acis with CU(II) and Diimine Ligands, Part 11. Amino Acids with O, N and S Functional Groups in the Side–Chain, Journal of Mass Spectrometry, vol. 30, pp. 1617–1627 (1995).
Rashed et al., Application of Electrospray Tandem Mass Spectrometry to Neonatal Screening, Seminars in Perinatology, vol. 23, No. 2 (Apr.), 1999, pp. 183–193.
Shindo et al., Identification of 17–Hydroxyprogesterone and Other Steriod Hormones in Saliva from a Normal Child and Patients with Congenital Adrenal Hyperplasia by Plasmaspray Liquid Chromatography/Mass Spectrometry, Biomedical Chromatography, vol. 4, No. 4, 1990, pp. 171–174.
Lai et al., Rapid Monitoring Assay of Congenital Adrenal Hyperplasia with Microbore High–Performance Liquid Chromatography/Electrospray Ionization Tandem Mass Spectrometry from Dried Blood Spots; Rapid Commun. Mass Spectrom. 2001: 15: pp. 2145–2151.
Seymour et al., Distinction and Quantitation of Leucine–Isoleucine Isomers and Lysine–Glutamine Isobars by Electrospray Ionization Tandem Mass Spectrometry (MS' n=2,3) of Copper(fl)–Diimine Complexes, J. Mass Spectrom, 35, pp. 566–571 (2000).
Simonsen et al., Technical Aspects of Neonatal Screening Using Tandem Mass Spectrometry. Report from the 4" Meeting of the International Society for Neonatal Screening,,4cta Paediatr Suppl. 1432: pp. 52–54, 1999.
Tandem Mass Spectrometry in Newborn Screening, Genetics in Medicine, Jul./Aug. 2000, vol. 2, No. 4, pp. 267–269.
Wilson et al., Bipyridyl Amino–Metal Complexes and Their Characteristics by Electrospray Mass Spectrometry, J Org. Chem. 1992, 5 7, pp. 6 941–6945.

* cited by examiner

Primary Examiner—Maureen M. Wallenhorst
(74) Attorney, Agent, or Firm—Sheridan Ross PC (57) ABSTRACT

Tandem mass spectrometry (MS/MS) has been used extensively for solving various biological problems, such as structure identification of oligopeptides, nucleic acids, and nucleotides. One of the main advances of MS/MS is that it lends itself to the quantitative and qualitative analysis of certain analytes and complex mixtures with little or no clean up. Quantitative analysis of amino acids and acylcarnitines using tandem mass spectrometry used to screen neonatal dried blood spot samples for disorders in the metabolism of amino acids, organic acids and fatty acids is an emerging technology. The method described herein extends the use of tandem mass spectrometry to the analysis of α-hydroxyketones and hexose phosphates from blood spots for newborn screening. Thus, according to this invention one test can be used to screen a number of neonatal disorders and diseases.

11 Claims, 7 Drawing Sheets m/e = 486  m/e = 353

ELECTROSPRAY TANDEM MASS SPECTROMETRY OF TRANSITION METAL DIIMINE COMPLEXES OF AMINO ACIDS, α-HYDROXYKETONES AND HEXOSE PHOSPHATES FOR NEWBORN SCREENING

The present invention relates to a method of identifying amino acids, α-hydroxyketones and hexose phosphates in the blood spots of newborns using elecrtospray tandem mass spectrometry. The present invention further relates to a novel method using a diimine metal ligand.

BACKGROUND OF THE INVENTION

Tandem mass spectrometry (MS/MS) has been used for several years to identify and measure carotene esters in blood and urine of children suspected of having inborn errors of metabolism. More recently, MS/MS has been used in pilot programs to screen newborns for conditions and disorders of amino and organic acids metabolism as well. A general overview of mass spectrometry, and in particular the tandem mass spectrometry and its use in newborn screening, can be found in "Tandem Mass Spectrometry in Newborn Screening" (ACGM/ASHG statement; Genetics and Medicine, July/August 2000, Volume 2, No. 4, page 267–269).

The current methodologies for tandem mass spectrometry screening use either butyl esters of the amino acids and acyl carnitine (Rashed M. S. et al. Sernin 1999: 25(2): 183–93) or direct underivatized analysis. The former causes degradation of some amino acid species and is very time consuming, and the latter suffers from insensitivity for some important amino acids.

Electrospray ionization of transition metal diimine ligand: α amino acid complexes has been demonstrated to provide sensitive determination of amino acid constituents of proteins in standard solutions (Gatlin, C. L. et al. J. Mass Spectrom 1995; 30: 1605–1616 and Gatlin, C. L. et al. J. Mass Spectrom 1995; 30: 1617–1627). However, there is a problem using this method in identifying homocystine or homocysteine to the same extent as the other amino acids. Thus, there is a need to improve the sensitivity of this method. In addition there is a need to extend the use of tandem mass spectrometry to include the identification of other compounds besides amino acids in the analysis. For example, congenital adrenal hyperplasia (CAH), a disorder caused by deficiency of the 21-hydrolase enzyme, is the most common inborn error of the adrenal steroid pathways. Early diagnosis and monitoring of CAH can be life saving. Monitoring and screening for CAH patients by measuring levels of 17 α-hydroxyprogesterone (17 OHP) or other steroids, has become a routine part of many programs. Numerous methods have been described to determine these steroid hormones, such as flourometry, radio immunoassay and high-performance liquid chromatography. A method for detecting 17 OHP using high-performance liquid chromatography/electrospray ionization tandem mass spectrometry was described by Lai et al. (Rapid Communication in Mass Spectrometry, 2001,15: 2145–2151) and Shindo et al. (Biomedical Chromatography, 1990, 4:171–174). Most of these methods, however, are affected by a degree of interference or cross-reactivity with other steroids.

In a further application, galactosemia is an inherited disorder wherein the metabolism of galactose caused by a deficiency of the enzyme galacatose-1 phosphate uridyl transferase. Galactosemia leads to accumulation of galacatose and galacatose-1 phosphate in blood and tissue and if left untreated, can result in neonatal death, or severe mental retardation, pyrosis of the liver and cardiacs. There are several available methods for neonatal screening for galactosemia. The simplest involves examining the urine for reducing substances. Other methods include activity assays for the enzyme galacatose-1 phosphate uridyl transferase and microbiological assays screening for galactose and galactose-1 phosphate. A method using tandem mass spectrometry is described by Jensen et al. (Clinical Chemistry, 2001, 74: 1364–1372.)

With the tandem mass spectrometry methods used to date, there is no single method that can be used to identify amino acids, α-hydroxyketones and hexose phosphates. This need is addressed in the present invention.

SUMMARY OF THE INVENTION

The present invention relates to a method of identifying amino acids, α-hydroxyketones and hexose phosphates in the blood spots of newborns using elecrtospray tandem mass spectrometry. The present invention further relates to a novel method using a diimine metal ligand.

Thus, according to the present invention, there is provided a method of new born screening for selected analytes using tandem mass spectrometry comprising the steps of: mixing a sample of blood or blood spot eluate with a metal diimine compound to form a metal diimine complex; subjecting said complex top high performance liquid chromatography to produce an eluate; subjecting the eluate from the HPLC step to an electrospray ion source of a mass spectrometer to yield MS/MS product ions; and detecting the MS/MS product ions.

BRIEF DESCRIPTION OF THE DRAWINGS

These and other features of the invention will become more apparent from the following description in which reference is made to the appended drawings wherein:

FIG. 8 shows the HPLC of copper bipyridyl complexes formed with extracts from CDC control blood spots. Top left chromatogram (FIG. 8A) is from a 10 nM 17α-Hydroxyprogesterone standard. Specimens (FIG. 8B) 300432 and 300521 (FIG. 8C) were considered negative for congenital adrenal hyperplasia. Specimen 300340 (FIG. 8D) was considered positive by Europe but negative by North American cutoffs. Specimens 300202 (FIG. 8E) and 300102 (FIG. 8F) were considered positive by North American and European cutoffs.

BRIEF DESCRIPTION OF THE INVENTION

The present invention relates to a method of identifying amino acids, α-hydroxyketones and hexose phosphates in the blood spots of newborns using electrospray tandem mass spectrometry in a single assay. The present invention further relates to a novel method using a diimine metal ligand.

Electrospray ionization of transition metal diimine ligand: α amino acid complexes has been demonstrated to provide sensitive determination of amino acid constituents of proteins in standard solutions. The low energy fragmentation of the radical cations is sufficiently informative to differentiate isomers such as leucine and isoleucine. According to the modifications made in this invention, this approach enables the sensitive determination of homocystine as well. According to the present invention, this improved method can also be used for the detection of the common acidic and neutral amino acids, α-hydroxyketones and hexose phosphates in newborn screening blood spots.

For neutral and acidic amino acids, this method gives signal intensities of 10 to 100 times those observed for the corresponding free amino acids. All of the essential amino acids produce unique parent-fragment ion combinations. Though the radical cations of the basic amino acids can be detected as both singly and doubly charged species, direct determination of the positive ions of the basic amino acids gives greater sensitivity. It is possible to detect the free positive ions of the acyl-carnitines in the presence of the transition metal diimine ligand reagent. The acyl-carnitines also form transition metal complexes in small amounts which produce informative mass spectra.

Selected transition metal ligand complexes of α-amino acids form spontaneously in aqueous and alcohol solutions with a very high association constant. This phenomenon enables a simple procedure for the processing of newborn screening blood spots. For example, the punched blood spot can be simply extracted in a solution containing methanol, water, metal salt and a diimine ligand. After elution of the blood spots, the eluate is aspirated directly into the tandem mass spectrometer. Approximately after 15 minutes of extraction, the eluates are measurable and remain stable for at least four hours.

According to the present invention, it has been found that this method of neonatal screening can at the same time detect 17 OHP and galactose 1-phosphate, markers for congenital adrenal hyperplasia and galactosemia, respectively. Transition metal ligand complexes of 17 OHP and galactose 1-phosphate are novel and electrospray tandem mass spectrometry of such complexes represent an improvement in using prior art methods. Not only can one test be used to identify a number of newborn disorders or diseases, thus combining three screening procedures into one, but the method is more sensitive than prior art methods.

According to the present invention the tandem mass spectrometry is combined with a HPLC rapid cleanup step. The cleanup step separates the transition metal ligand complexes from other complexes and ions such as sodium, potassium and chloride present in the sample. These complexes and ions compete with the transition metal ligand complexes for ionization during the electrospray process and can substantially suppress the signal strength of the ions of interest.

According to the present invention, the metal salt which can be used is selected from the group consisting of: copper, nickel, cadnium, iron, cobalt and zinc. In the case of the copper ligand complexes, the existence of the two abundant copper isotopes which differ by two mass units enables the confirmation of the presence of a transition metal complex. This is useful for method development and may also be useful in routine clinical use. For difficult quantitative situations, the ion abundances from the fragmentations due to both copper isotopes can be summed to improve sensitivity or ratioed to improve specificity. In the interest of overall sensitivity, it may ultimately be preferred to use mono-isotopically pure copper in the reagent. This would be feasible because only minute amounts of copper are used in the reagent.

The diimine ligand, which can be used according to the present invention are well known in the art. They can for example be selected from either 2,2'-bipyridyl or 1,10-phenantroline, including modified forms of said compounds.

The samples used in new born screening are usually blood spots, obtained from the newborn patient, by spotting blood onto a filter paper. The sample usually comprises a punch hole sample from the filter paper.

The punched samples are extracted with a metal diimine solution in methanol/water. The methanol/water ratio ranges from 80:20 to 95:5. Typically the metal diimine concentration is about 100 $\mu$M in methanol/water. The method is a modification of the method disclosed in Gatlin et al. 1995 (J. Mass Spectrom 30: 1605–1616).

HPLC was performed using a C-18 reverse phase column using methanol/water as the solvent. The HPLC eluate was directly introduced into an ion spray source of the elctrospray tandem mass spectrometer. Analytes were detected using the Multiple Reaction Monitoring mode (MRM) in which ion pairs, corresponding to the parent and daughter ions of each fragmentation (Q1 and Q3 m/e settings) were monitored.

As noted previously, prior art methods using metal and diimine ligands to form an amino acid complex, have not been useful for the identification of cysteine and cystine. Cysteine differs from the other amino acids in that it does not give the corresponding $[Cu(II)cys-H)L]^+$ ion, but is partially oxidized by Cu(II) in solution to give cystine. Some of the cystine forms a complex with the copper and diimine ligand.

However, it was discovered that the oxidized form of the thiol amino acids could be readily detected as their transition metal diimine complexes. In the neonatal screen homocystinuria can be detected by determining blood spot levels of homocystine.

Congenital adrenal hyperplasia (CAH), a disorder caused by deficiency of the 21-hydrolase enzyme, is the most common inborn error of the adrenal steroid pathways. Early diagnosis and monitoring of CAH can be life saving. Monitoring and screening for CAH patients by measuring levels of 17 α-hydroxyprogesterone (17 OHP) or other steroids, has become a routine part of many programs. 17 α-hydroxyprogesterone from blood spot extracts was negligible when the extract was aspirated directly with the metal diimine reagent. This was likely due to competing ionization. However, the complex could be readily detected at 10 nM after a rapid HPLC sample cleanup using the metal diimine reagent in methanol: water as the mobile phase, as described above.

Other steroids can also be detected according to the method of the present invention. These steroids can include, but are not limited to: deoxycorticosterone, pregnenolone, 17-hydroxypregnenolone and cortisol.

Galactosemia is an inherited disorder wherein the metabolism of galacatose caused by a deficiency of the enzyme galacatose-1 phosphate uridyl transferase. Galactosemia leads to accumulation of galacatose and galacatose-1 phosphate in blood and tissue and if left untreated, can result in neonatal death, or severe mental retardation, cirrohosis of the liver and cardiacs. It was found, according to the modifications of the present invention, that galacatose-1 phosphate can also be detected. Other hexose phosphates, that can be detected according to the present invention include, for example: fructose 1-phosphate and glucose 1-phospate.

The present invention will now be described with reference to certain examples which are not to be construed as limiting.

EXAMPLES

Example 1

Detection of Homocystine

All chemicals were reagent grade and >99% purity unless otherwise stated. Solvents were HPLC grade and water was ASTM type II with resistivity >18 MΩ. Homocystine was from Sigma Chemical (St Louis Mo). Control Blood Spots were from the Centers for Disease Control Newborn Screening Quality Assurance program.

Copper bipyridyl complexes were prepared in situ using modifications to the method for aminoacids developed by Gatlin et al (1). Specifically the corresponding compound was added to a solution of equimolar amounts of copper sulphate and 2,2'-bipyridyl. Typically the copper sulphate and 2,2'-bipyridyl concentration was 100 $\mu$M in methanol::water solutions, in the proportion 90:10 v:v. Blood spots were sampled with two $\frac{1}{8}$" punched holes. The punched samples were extracted with copper bipyridyl reagent (50 $\mu$l) for 15 minutes prior to analysis.

Mass spectrometry was performed on an Applied Biosystems/MDS Sciex API 2000 tandem mass spectrometer equipped with Turbulon® electrospray ion source. Samples were introduced either by infusion using the SCIEX syringe pump with flow rates of 20 $\mu$L/min or by injection into a solvent stream using a Perkin Elmer series 200 Autosampler equipped with Rheodyne Model 7725 injector with a 20 $\mu$L loop. Solvents were pumped using a Shimadzu Model LC10AD HPLC pump. HPLC was performed using a C-18 reverse phase column and a solvent flow of 300 $\mu$L/min. The HPLC eluate was directly introduced into the Ionspray source using the Turbulon® Spray heated to 300° C. with a nitrogen nebulizing gas setting of 60 mmHg.

MS parent ion scans, MS/MS product ion scans and MS/MS optimization for each analyte were performed while infusing a solution containing the analyte (typically at a concentration of 25 $\mu$M) and the copper bipyridyl complex in methanol:water 1:1.

Electrospray ionization was performed in positive ion mode with capillary potentials of 4000–5000 eV. Collision induced (CAD) dissociations were carried out in the middle hexapole region using Nitrogen as the collision as. Typical collision energies were from 15–40.

Flow injection and HPLC analyses of 20 $\mu$L used sample volumes. Analytes were detected using the Multiple Reaction Monitoring mode (MRM) in which ion pairs, corresponding to the parent and daughter ions of each fragmentation (Q1 and Q3 m/e settings) were monitored.

Aquired data were processed on a MAC G3 system using the Applied Biosystems/MDS Sciex tuning and sample control software.

Figure 1:
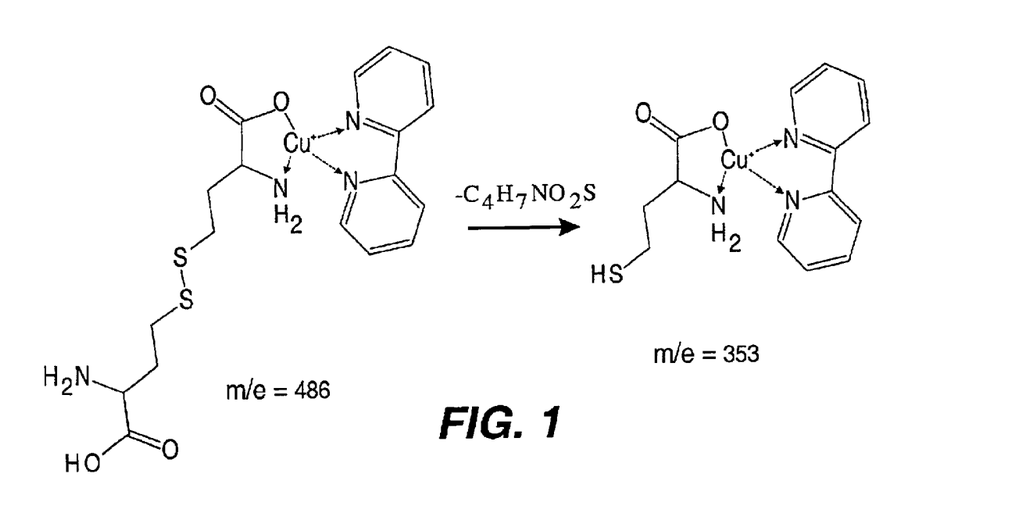
FIG. 1 shows the fragmentation of copper bipyridyl complex with homocystine.
Figure 5:
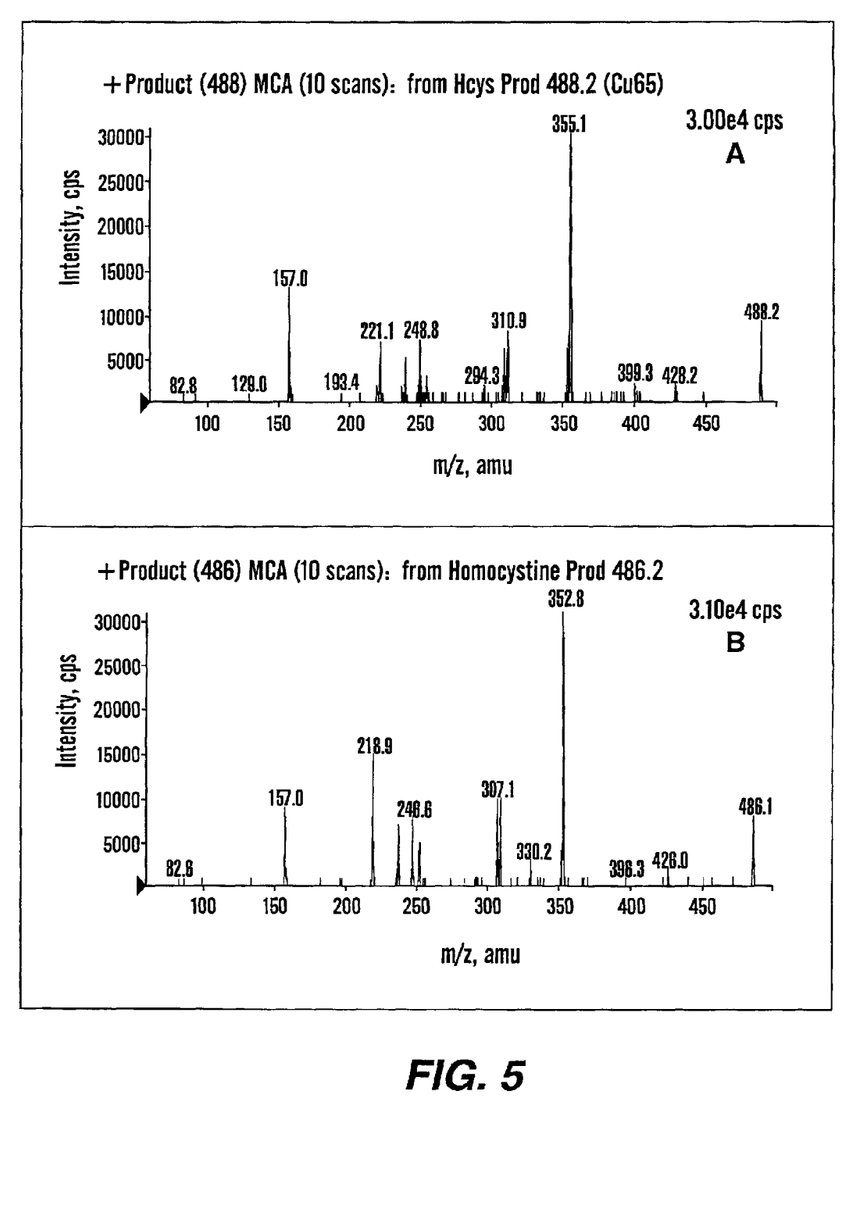
FIG. 5 shows CAD product ion scan of the copper bipyridyl complex of homocystine (product of 486 contains $^{63}Cu$ (FIG. 5A) and products of 488 contain $^{65}CU$ (FIG. 5B)).

The single quadrupole electrospray mass spectrum of a 50 $\mu$M solution of homocystine with copper bipyridyl reagent showed prominent ions at m/e 486.1 and 488.1. The ion abundances were in the ratio of 69.2:30.8 which corresponds to the natural abundance of the stable isotopes of copper. The ions correspond to the copper bipyridyl complex with homocystine, designated [CuII(Hcys-H)(bpy)] $^{+\cdot}$(FIG. 1). CAD of the putative complex ion of m/e 486.1, at the relatively low energy of 25 eV, resulted in the formation of a fragment at m/e 353.0 which corresponds to the ion [CuII(Hcys-$C_4H_7NO_2S$)(bpy)] $^{+\cdot}$. This fragmentation corresponds to cleavage at the disulfide bond with loss of $C_4H_7NO_2S$. The ion corresponding to the $^{65}$Cu complex at m/e 355.0 was formed from CAD of the ion of mass 488.1. The CAD product of $^{63}$Cu and $^{65}$Cu complexes are shown in FIGS. 5A and 5B.

The Homocystine copper bipyridyl complex could be readily detected at 5 $\mu$M after a rapid HPLC sample cleanup using copper bipyridyl reagent (50 $\mu$M in Methanol:Water 95:5 v:v) as the mobile phase. Recovery of 15 $\mu$M Homocystine added to blood spots was 70–90%

Example 2

Detection of Galactose-1-Phosphate

The mass spectrometry was done as described above in Example 1. Galactose-1 phosphate was obtained from Sigma Chemical (St. Louis Mo.).

Figure 2:
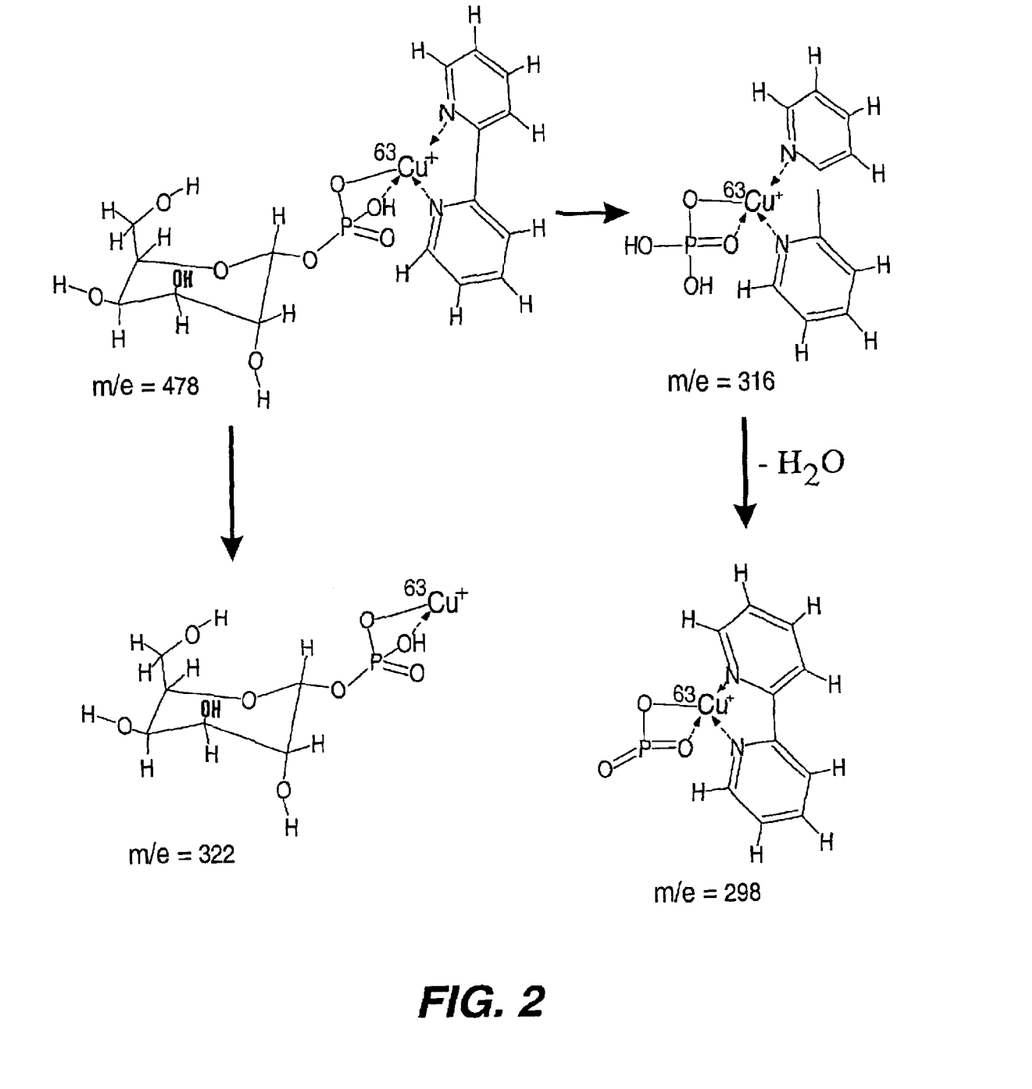
FIG. 2 shows the fragmentation of copper bipyridyl complex with glactose-1-phosphate.
Figure 7:
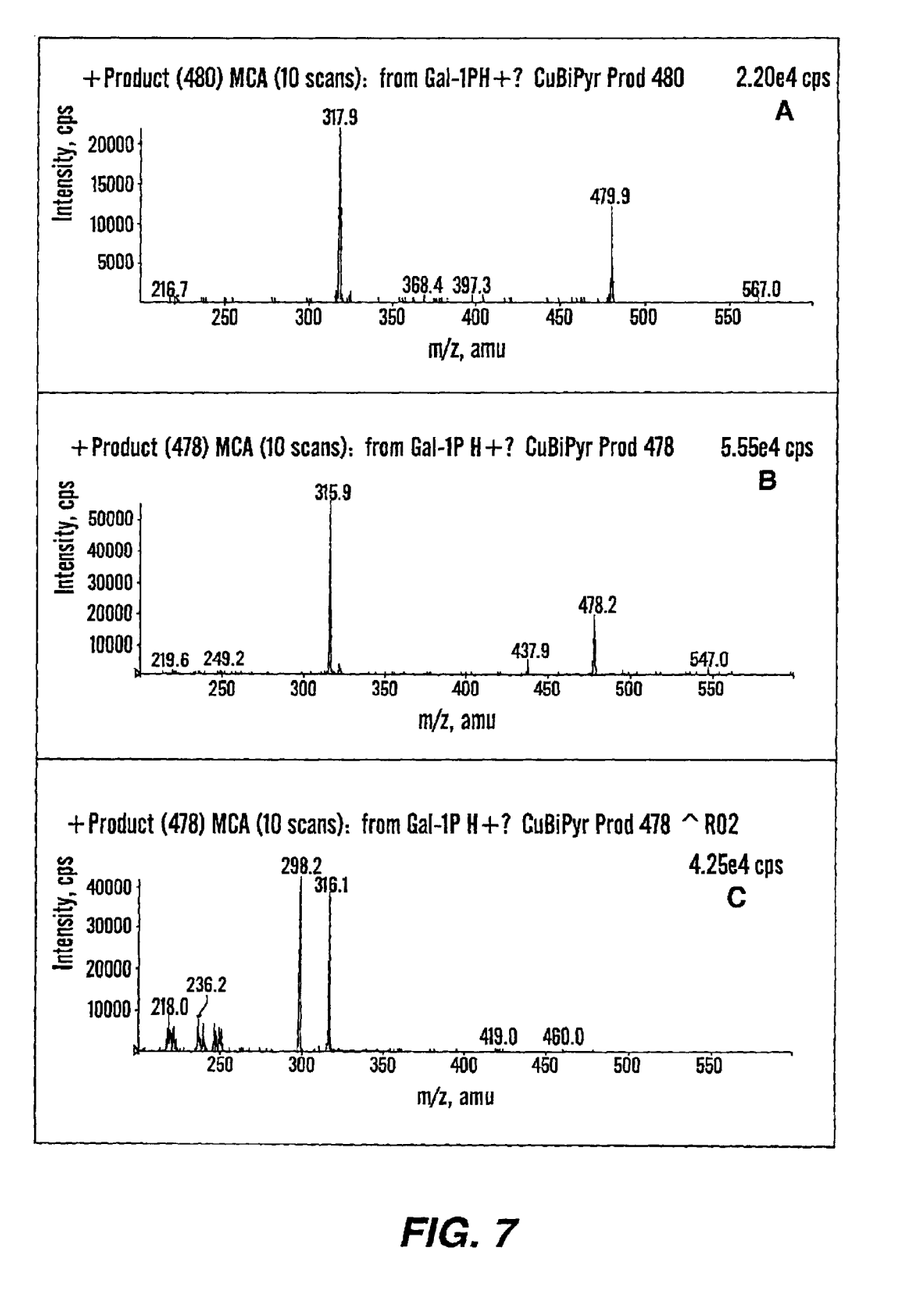
FIG. 7 shows the CAD product ion scan of the copper bipyridyl complex of galactose-1-phosphate (products of 478 contains $^{65}CU$ (FIG. 7A) and products of 480 contain $^{65}CU$ (FIG. 7B)). The bottom panel (FIG. 7C) shows the CAD spectrum at high collision energies.
Figure 8:
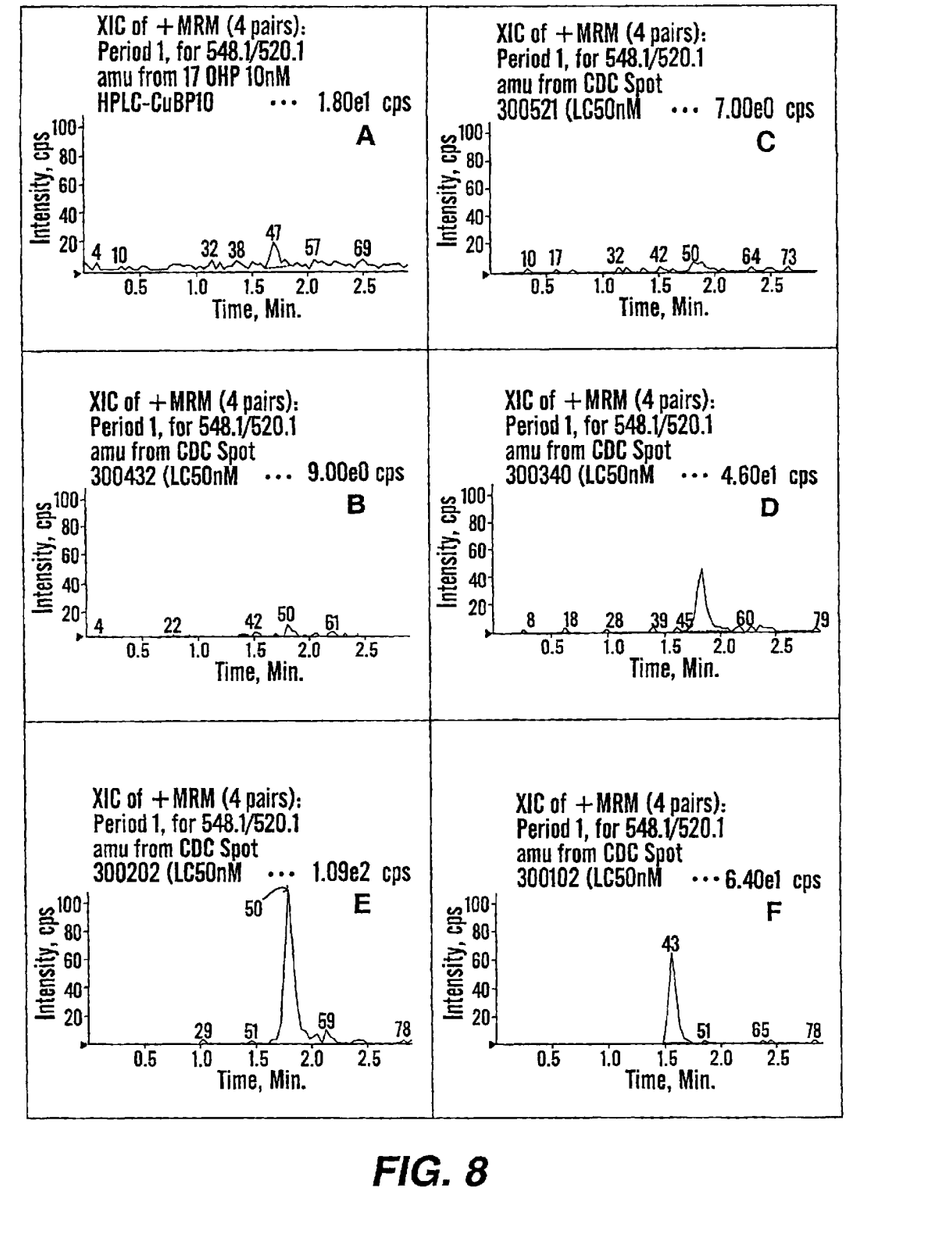

The single quadrupole electrospray mass spectrum of a 10 $\mu$M solution of Galactose-1 Phosphate with copper bipyridyl reagent showed ions at m/e 478.0 and 480.0. The ion abundances were in the ratio of 69.2:30.8 which corresponds to the natural abundance of the stable isotopes of copper. The ions correspond to the copper bipyridyl complex with Galactose-1-Phosphate, designated [CuII((Gal-1-P)-H)(bpy)]$^{+\cdot}$ (FIG. 2). The sodium and potassium adducts [CuII((Gal-1-P-Na)-$H_2$)(bpy)]$^{+\cdot}$ [CuII((Gal-1-P-K)$H_2$)(bpy)]$^{+\cdot}$ were more prominent than the free acid form. CAD of the putative complex ion of m/e 478.0, at an energy of 30 eV, resulted in the formation of an abundant fragment at m/e 316.0, which corresponds to the ion [CuII(Gal-1-P-$C_7H_{15}O_5$)(bpy)]$^{+\cdot}$, and a much less abundant fragment at m/e 322.0. The latter corresponds to the ion [CuII(Gal-1-P-H)]$^{+\cdot}$ formed from the loss of bipyridyl. Increasing the collision energy to 55 eV produced a fragment at m/e 298 which corresponds to the ion [CuII(Gal-1-P-$C_7H_{13}O_4$)(bpy)]$^{+\cdot}$. The ion at m/e 480 gave the corresponding fragments at two mass units higher which indicated that these fragments all contain Copper atoms. The CAD product ion scan of the copper bipyridly complex of galactose-1-phosphate (products of 478 contains $^{65}$CU is shown in FIG. 7A and products of 480 contain $^{65}$CU is shown in FIG. 7B. FIG. 7C shows the CAD spectrum at high collision energies.

The free acid complex could be readily detected at 1.0 $\mu$M using MRM after a rapid HPLC sample cleanup using copper bipyridyl reagent as the mobile phase. The ion abundance for the MRM 478/316 was 1×10$^5$ cps. Rapid HPLC removed the interfering cations since the sodium and potassium adducts could not be detected. Response was linear in the range 0.8–1.6 $\mu$M.

Example 3

Detection of 17α-Hydroxyprogesterone and Deoxycorticosterone

The mass spectrometry was done as described above in Example 1. Progesterone, deoxycorticosterone and 17

α-hydroxyprogesterone were obtained from Sigma Chemical (St. Louis Mo.).

Figure 3:
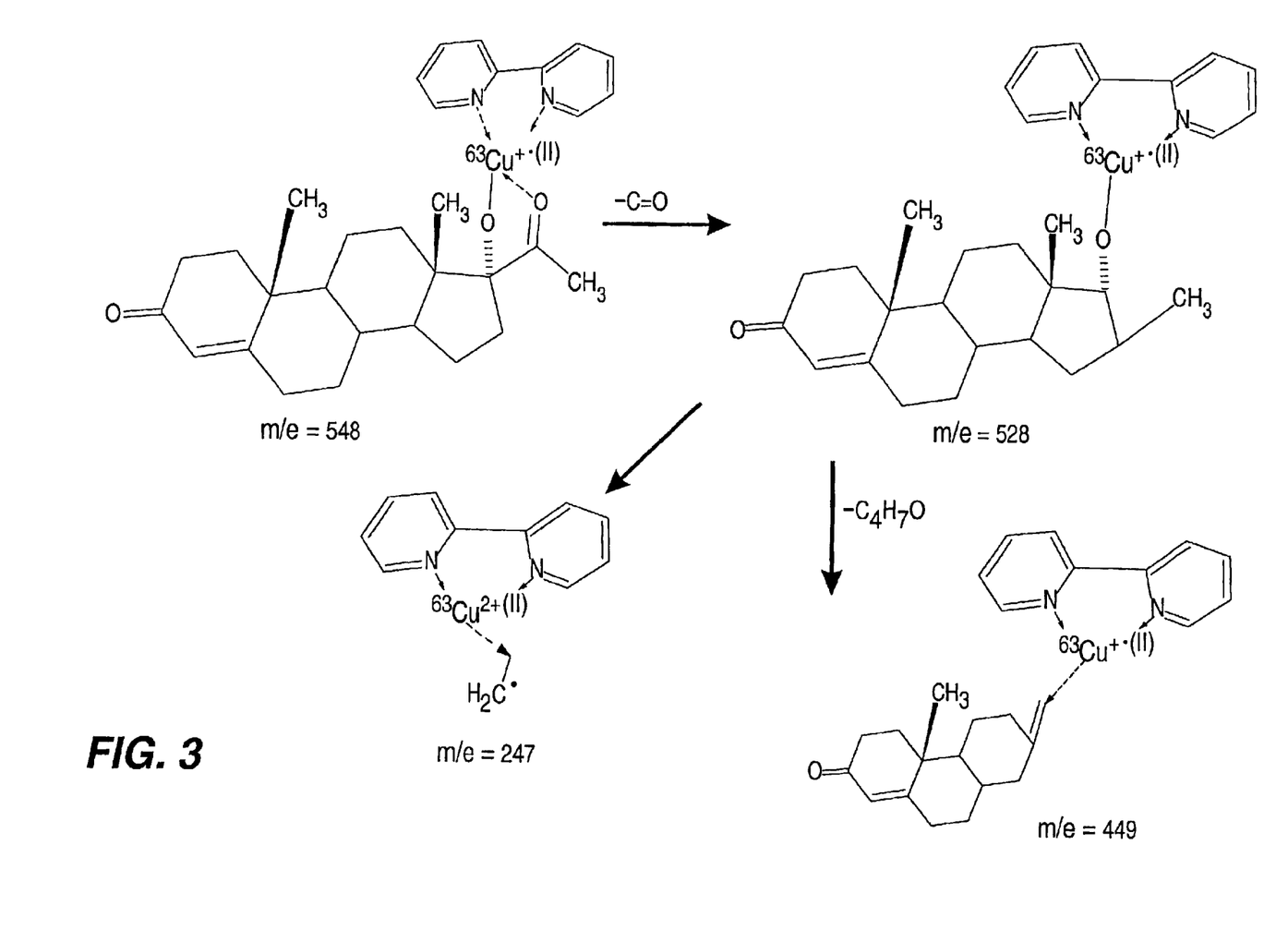
FIG. 3 shows the fragmentation of copper bipyridyl complex with 17-α-hydroxyprogesterone.
Figure 6:
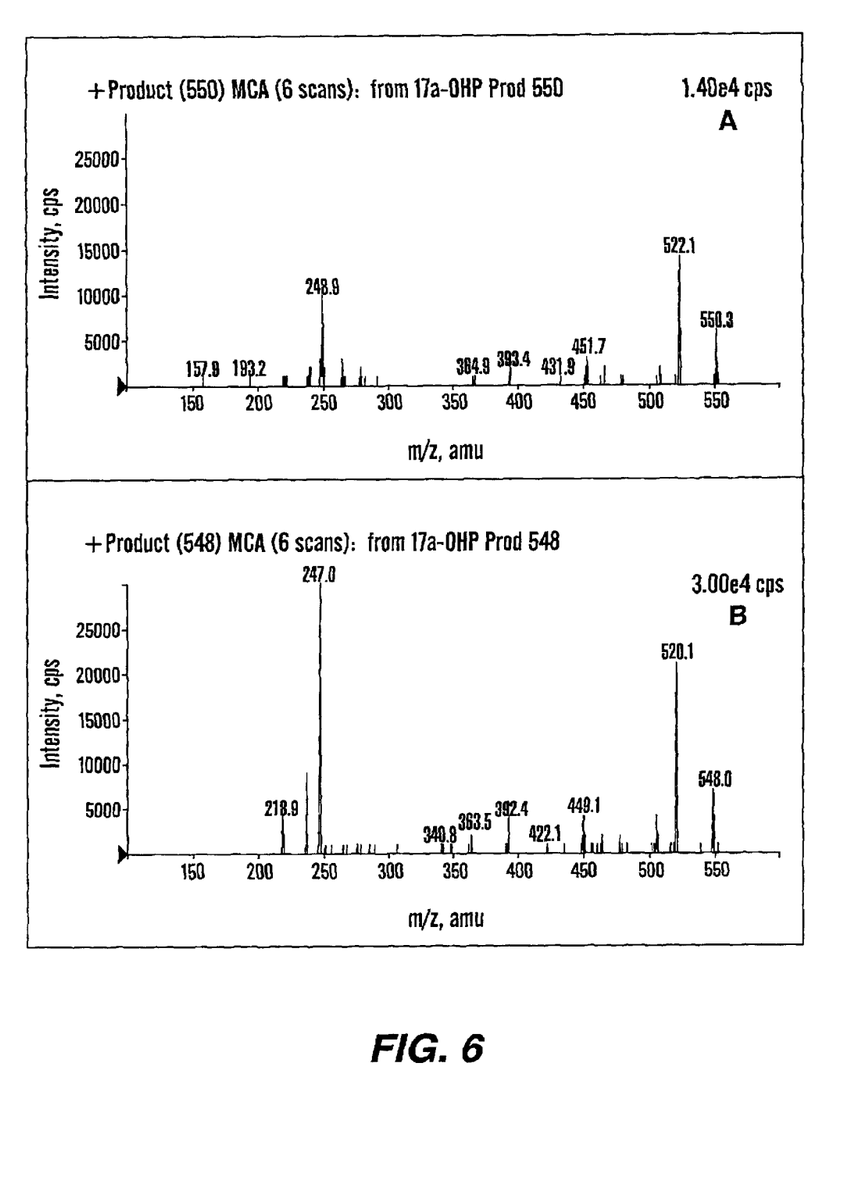
FIG. 6 shows the CAD product ion scan of the copper bipyridyl complex of 17-α-hydroxyprogesterone (products of 548 contains $^{63}CU$ (FIG. 6A) and products of 550 contain $^{65}CU$ (FIG. 6B)).

The single quadrupole electrospray mass spectrum of a 1 μM solution of 17α-Hydroxyprogesterone with copper bipyridyl reagent showed ions at m/e 548.0 and 550.0. The ion abundances were in the ratio of 69.2:30.8 which corresponds to the natural abundance of the stable isotopes of Copper. These ions correspond to the copper bipyridyl complex with 17α-Hydroxyprogesterone, designated [CuII((17OHP)-H)(bpy)]$^{+\cdot}$ (FIG. 3). CAD of the putative complex ion of m/e 548.0, at an energy of 30 eV, resulted in the formation of a prominent fragment at m/e 520.0, which corresponds to the ion [CuII(17OHP-COH)(bpy)]$^{+\cdot}$. This fragment arises from the loss of carbon monoxide. Because this is a rare neutral loss the background was extremely low which enabled detection of 17α-hydroxyprogesterone at levels as low as 2 nM in standard solutions and as low as 20 nM in blood spots. The ion at m/e 550 gave the corresponding fragment at m/e 522.0, two mass units higher, which indicated that this fragment still contains a copper atom. Other copper containing fragments included m/e 449 corresponding to the ion [CuII((17OHP)-C$_5$H$_8$O$_2$)(bpy)]$^{+\cdot}$ and m/e 247 corresponding to [CuII(C2H3(bpy)]$^{+\cdot}$. The CAD product ion scan of the copper bipyridly complex of 17-α-hydroxyprogesterone (products of 548 contains $^{63}$CU is shown in FIG. 6A and products of 550 contain $^{65}$CU is shown in FIG. 6B.

Competing ionization resulted in very low recoveries from blood spots, thus ion removal by rapid HPLC cleanup was required to yield acceptable recoveries.

Figure 4:
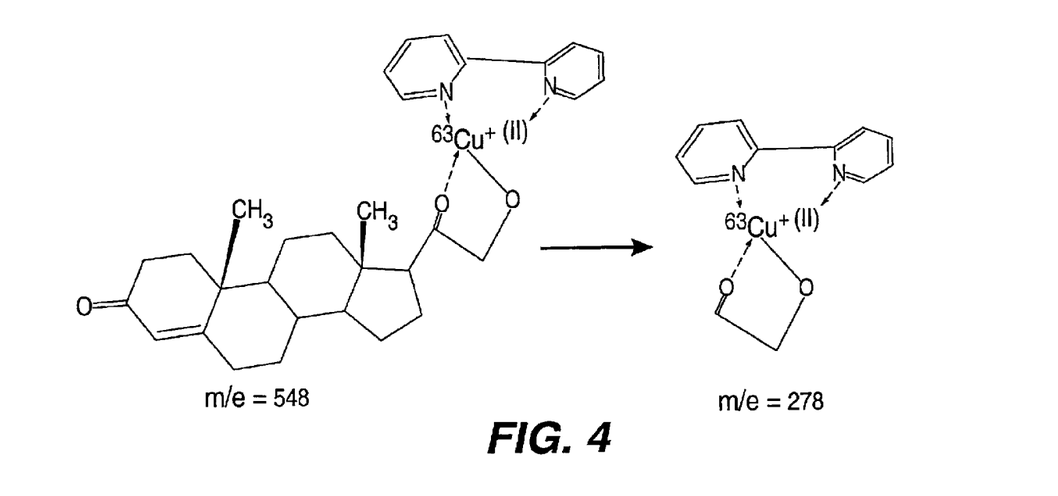
FIG. 4 shows the fragmentation of copper bipyridyl complex with deoxycorticosterone.

The isomeric deoxycorticosterone also formed a complex with copper bipyridyl reagent with masses of 548 and 550[CuII(DEOC-H)(bpy)]$^{+\cdot}$. However the complex with deoxycorticosterone did not loose carbon monoxide upon fragmentation but instead lost the entire steroid ring to give the fragment m/e 278[CuII(C$_2$H$_3$O$_2$)(bpy)]$^{+\cdot}$. (FIG. 4). The complex with deoxycorticosterone did not lose carbon monoxide upon CAD but instead the bond between C17 and C20 cleaved with resulting loss of the steroid moiety. Thus deoxycorticosterone will not interfere with the measurement of 17α-Hydroxyprogesterone.

Recoveries of 17α-Hydroxyprogesterone from blood spot extracts were negligible when the extract was aspirated directly with the copper bipyridyl reagent. This was likely due to competing ionization. However, the complex could be readily detected at 10 nM after a rapid HPLC sample cleanup using copper bipyridyl reagent (50 μM in Methanol:Water 95:5 v:v) as the mobile phase. The ion abundance for the MRM 548/520 was 1×10$^2$ cps.

Two blood spots from the CDC quality assurance program for congenital adrenal hyperplasia, which were considered positive by the North American Screening criteria had detectable levels of 17α-Hydroxyprogesterone using the HPLC procedure. One blood spot with levels below the North American cutoff but above the European cutoff also had detectable levels of 17α-Hydroxyprogesterone. The two negative blood spots, by both criteria, had undetectable levels of 17α-Hydroxyprogesterone. These results are shown in FIGS. 8A to 8F.

All scientific references and patents are incorporated herein by reference.

The present invention has been described with regards to preferred embodiments. However, it would be obvious to a person skilled in the art that a number of variations and modifications can be made without departing from the scope of hte invention as described in the following claims.

The embodiments of the invention in which an exclusive Property of privilege is claimed are defined as follows:

1. A method of new born screening for selected analytes using tandem mass spectrometry comprising the steps of:
   mixing a sample of blood from a newborn with a metal diimine compound to form a transition metal diimine complex;
   subjecting said complex to high performance liquid chromatography (HPLC) to separate the transition metal diimine complex from other complexes and ions and to produce an eluate;
   subjecting the eluate from the HPLC step to an electrospray positive ion source of a mass spectrometer to yield MS/MS product ions; and
   detecting the MS/MS product ions as a measure of the selected analytes.

2. The method of claim 1 wherein the selected analytes are selected from the group consisting of an amino acid, an α-hydroxyketone and a hexose phosphate.

3. The method of claim 2 wherein the α-hydroxyketone is selected from the group consisting of 17 α-hydroxyprogesterone, deoxycorticosterone, pregnenolone, 17α-hydroxypregnenolone and cortisol.

4. The method of claim 3 wherein the α-hydroxyketone is 17 α-hydroxyprogesterone.

5. The method of claim 2 wherein the hexose phosphate is selected from the group consisting of galacatose-1 phosphate, fructose 1-phosphate and glucose 1-phosphate.

6. The method of claim 5 wherein the hexose phosphate is galacatose-1 phosphate.

7. The method of claim 1 wherein the diimine compound is selected from the group consisting of 2,2'-bipyridyl, 1,10-phenantroline, and modified forms thereof.

8. The method of claim 1 wherein the metal is selected from the group consisting of copper, nickel, cadmium, iron, cobalt and zinc.

9. The method of claim 1 wherein the metal diimine compound is dissolved in a methanol water solution.

10. The method of claim 9 wherein the methanol water solution has a ratio of methanol to water from about 80:20 to about 95:5.

11. A method of new born screening for an analyte, including an amino acid, an α-hydroxyketone and a hexose phosphate, using positive ion mode tandem mass spectrometry comprising the steps of:
    mixing a sample of blood from a newborn with a copper dipyridyl complex to form an analyte transition copper dipyridyl complex;
    subjecting said complex to high performance liquid chromatography (HPLC) to separate the transition copper bipyridyl complex from other complexes and ions and to produce an eluate;
    subjecting the eluate from the HPLC step to an electrospray positive ion source of a mass spectrometer to yield MS/MS product ions; and
    detecting the MS/MS product ions as a measure of the analytes.

* * * * *

UNITED STATES PATENT AND TRADEMARK OFFICE
CERTIFICATE OF CORRECTION

PATENT NO. : 6,800,489 B2
DATED : October 5, 2004
INVENTOR(S) : Kent C. Dooley

It is certified that error appears in the above-identified patent and that said Letters Patent is hereby corrected as shown below:

<u>Title page,</u>
Item [73], Assignee, should read -- Izaak Walton Killam Health Centre, Halifax (CA) --

Signed and Sealed this

Eighth Day of February, 2005

JON W. DUDAS
*Director of the United States Patent and Trademark Office*